(12) United States Patent
Sorg

(10) Patent No.: US 7,753,867 B2
(45) Date of Patent: Jul. 13, 2010

(54) DEVICE TO ALLEVIATE THE SYMPTOMS OF RESTLESS LEG SYNDROME, RESTLESS ARMS SYNDROME, AND FOOT AND LEG CRAMPS

(76) Inventor: Mary M. Sorg, 2210 Elk Creek Rd., Waterford, PA (US) 16441

( * ) Notice: Subject to any disclaimer, the term of this patent is extended or adjusted under 35 U.S.C. 154(b) by 844 days.

(21) Appl. No.: 11/307,052

(22) Filed: Jan. 20, 2006

(65) Prior Publication Data

US 2009/0024066 A1    Jan. 22, 2009

(51) Int. Cl.
*A61F 13/06* (2006.01)
*A61F 5/30* (2006.01)
*A43B 13/38* (2006.01)
*A43B 19/00* (2006.01)
*A61F 5/14* (2006.01)

(52) U.S. Cl. .............. 602/66; 602/60; 602/61; 602/62; 602/63; 128/112.1; 128/882; 36/43; 36/71; 36/140; 36/145; 36/150

(58) Field of Classification Search ........ 602/2, 602/6, 27, 53, 62, 65, 75, 79, 60, 61, 63, 602/66; 36/140, 43, 71, 145, 150; 128/95.1, 128/99.1, 100.1, 112.1, 882; 2/61, 239–241
See application file for complete search history.

(56) References Cited

U.S. PATENT DOCUMENTS 1,651,285 A    11/1927    Levick (Continued)

FOREIGN PATENT DOCUMENTS

DE    19638349    3/1998

(Continued)

OTHER PUBLICATIONS

Norman, Wesley. "Sole of Foot". The Anatomy Lesson ©1999. <http://home.comcast.net/~WNOR/soleoffoot.htm>.*

(Continued)

*Primary Examiner*—Patricia M Bianco
*Assistant Examiner*—Keri J Nicholson
(74) *Attorney, Agent, or Firm*—Jon L. Woodard; MacDonald Illig Jones & Britton LLP

(57) ABSTRACT

A flexible foot relief pad that is wrapped about and secured to the individual's foot in order to relieve the symptoms of restless leg syndrome, restless arms, and foot and leg cramps includes a pliable cloth wrap having a foot engaging portion joined to a securing portion by a fold, with the foot engaging portion enclosing a cavity for holding therein a layered raised pressure application pad that applies pressure to select areas of the inner side and sole of the foot with the layered pad configured so that a portion of the pad extends transverse to the sole of the foot and a raised portion extends along the inner side of the foot for applying pressure to the specific muscle groups involved in restless leg syndrome. The flexible foot relief pad also includes adjustable securement members that wrap around and encompass both the foot and the relief pad for securing the pad to the foot, and the point of attachment for each securement member is adjustable thereby providing for the even application of pressure against the specific areas of the sole of the foot or for varying the amount of pressure applied to such areas on the sole of the foot.

47 Claims, 6 Drawing Sheets

U.S. PATENT DOCUMENTS

| | | | |
|---|---|---|---|
| 2,027,055 A | 1/1936 | Mirenta | |
| 2,884,719 A | 5/1959 | Crompton | 36/71 |
| 3,588,917 A | 6/1971 | Antonious | 2/161 |
| 4,476,858 A | 10/1984 | Curtis | 128/80 |
| 4,747,410 A | 5/1988 | Cohen | 128/581 |
| 5,129,395 A | 7/1992 | Hoffmann | 36/145 |
| 5,554,107 A | 9/1996 | Shannahan | 602/66 |
| 5,735,804 A | 4/1998 | Chan | 601/136 |
| 6,141,890 A | 11/2000 | Chtn | 36/147 |
| 6,146,348 A * | 11/2000 | Slautterback | 602/21 |
| 6,393,736 B1 | 5/2002 | Greer, Jr. et al. | 36/155 |
| 6,415,795 B1 | 7/2002 | Kew | 128/869 |
| 6,558,339 B1 | 5/2003 | Graham | 602/66 |
| 6,699,209 B2 | 3/2004 | Turtzo | 602/27 |
| 2005/0251073 A1 | 11/2005 | Roth | |

FOREIGN PATENT DOCUMENTS

| | | |
|---|---|---|
| EP | 0679377 | 11/1995 |

OTHER PUBLICATIONS

European Search Report for European Application No. 06840141.3-2310 dated Feb. 4, 2010.

Text of First Office Action for Chinese Application (No. 20100224400938480) dated Mar. 1, 2010 with English translation attached.

\* cited by examiner

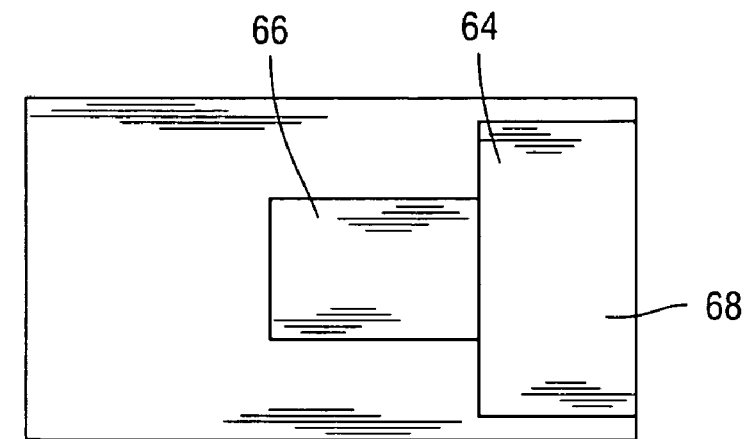
*Fig.7*
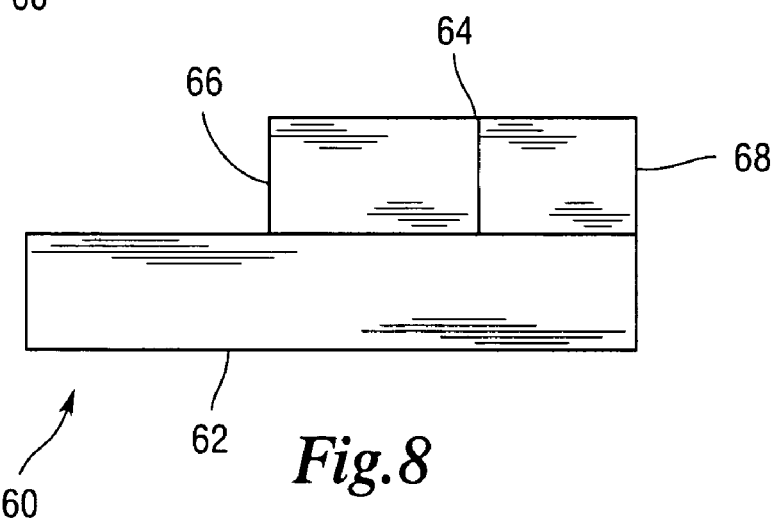
*Fig.8*
*Fig.9*

DEVICE TO ALLEVIATE THE SYMPTOMS OF RESTLESS LEG SYNDROME, RESTLESS ARMS SYNDROME, AND FOOT AND LEG CRAMPS

BACKGROUND OF THE INVENTION

The foot is one of the most complicated and sophisticated of all body parts or appendages, and yet its care and maintenance is generally neglected until an affliction or injury occurs, and then the realization supervenes that this is an appendage whose proper functioning is a sine qua non of a healthy, active life.

The afflictions, maladies and injuries that can occur to the foot are many. One type of injury that can occur is metatarsalgia—a type of foot pain that occurs in the ball of the foot and that can impede walking and standing. Another affliction is excess pronation—a problem that occurs as part of the process of human gait and which if untreated can lead to progressive bone deformities. A common foot disorder that causes heel spur and other types of plantar facial pain is plantar fasciitis. Relaxing the musculature of the foot commonly treats plantar fasciitis, and this can be accomplished using braces and splints of various designs. It is often the case that the arch of the foot requires support, and thus arch support orthotics can be disposed upon the inner sole of the shoe for building up the shoe thereby supporting the arch of the foot. For providing comfort to the sole of the foot placing a massaging pad on the inner sole of the shoe is a relatively simple and inexpensive expedient.

An affliction of amorphous etiology is restless leg syndrome that can manifest itself in various ways such as by ineluctable creeping sensations and internal itching sensations occurring in the lower extremities. Generally symptoms are more pronounced at the end of the day when the individual is seated or in bed. One way to obtain at least some relief is for the individual to move his or her legs—often for some period of time. However, it is quite common that restless leg syndrome can occur for long periods of time, such as throughout the night, thus frustrating and impeding any possibility of the individual attaining a sound and restful sleep.

Thus, the prior art discloses a range of devices to treat and alleviate the many foot afflictions and ailments.

For example, the Compton patent (U.S. Pat. No. 2,884,719) discloses a device for the relief and prevention of metatarsalgia and includes a support pad comprised of two layers of material with the support pad aligned with and conforming to the inside edge of the shoe so that the weight of the three adjacent metatarsal heads can be redistributed.

The Hoffman patent (U.S. Pat. No. 5,129,395) discloses a shoe insert for preventing excess pronation that is designed to fit the area of void on the plantar side of the human foot and includes a central portion bounded by a convex portion and sloping portions.

The Shanahan patent (U.S. Pat. No. 5,554,107) discloses an elastic foot wrap that is composed of elastic material and includes several toe openings and an ankle opening and which is used for treating plantar fasciitis.

The Chan patent (U.S. Pat. No. 5,735,804) discloses a massaging foot pad for disposition in a shoe or sandal and which includes protrusions arrayed upon a sheet with the protrusions elongated in a horizontal direction and slanted in an orthogonal direction that depress during the downward step and rebound when the foot lifts up off the ground.

The Chtn patent (U.S. Pat. No. 6,141,890) discloses a sole pad unit for supporting the metatarsal bone and massaging the center of the sole of the foot and includes an l-shaped massage block mounted on the sole pad unit and capable of depressing under the pressure of the foot, with the massage block having vents to allow for airflow circulation therethrough.

The Greer Jr. et al. patent (U.S. Pat. No. 6,393,736 B1) discloses an adjustable arch brace orthotic that includes a plurality of adjustable cantilevered extensions that are adjustable by a tensioning means built into the orthotic to vary the arch curve slope and height so that the user's arch can be therapeutically supported.

The Graham patent (U.S. Pat. No. 6,558,339 B1) discloses a foot elevator to alleviate heel and arch pain, and which includes a brace in the form of a semi-elastic bandage that supports the heel and arch of the foot.

The Turtzo patent (U.S. Pat. No. 6,699,209 B2) discloses a foot splint for the treatment of plantar fasciitis that includes a foot plate on which the sole of the foot rests with the proximal and distal portions upwardly angled and securing means that wrap around the foot for attaching the splint thereto.

Nonetheless, despite the ingenuity of the above devices, there remains a need for a device that alleviates the symptoms of restless leg syndrome and which can be unobtrusively worn on the individual's feet for applying pressure over extended periods of time while the individual is recumbent or relaxing in a chair.

BRIEF SUMMARY OF THE INVENTION

The present invention comprehends a flexible foot relief pad that is wrapped around the individual's foot to alleviate the symptoms associated with restless leg and restless arms syndrome and also may be used to alleviate foot and leg cramps. The flexible foot relief pad includes a cloth wrapping member that defines a securing portion and a foot engaging or contacting portion with a fold or crease joining the foot engaging portion to the securing portion. The cloth wrapping member is two sided and defines a continuous outer surface and an opposite continuous inner surface. The foot engaging portion of the cloth wrapping member encloses a cavity, and disposed within the cavity is a raised pressure application pad generally of two layers. The first layer is a rectangular base pad that fills the cavity and the second layer is a T-shaped pad that sits on the rectangular pad. The crossbar of the T-shaped pad is parallel with the fold or crease so that when the flexible foot relief pad is wrapped about the individual's foot the crossbar extends along the inner side of the individual's foot and applies specific pressure to the flexor hallucis breves and the abductor hallucis muscles. In order to secure the flexible foot relief pad on the foot, at least one, and preferably several, VELCRO® straps extend along the outer surface with a substantial portion of the straps extending beyond the securing portion so that the straps can fully encompass the foot and loop back for attachment to the foot engaging portion thereby securing the flexible pad to the foot. Because the straps incorporate VELCRO® material, the point of attachment for each strap when the straps are looped back is variable thus allowing the individual to vary or adjust the pressure that is applied to the muscles across the sole of the foot by the multi-layered raised pad, and also to the muscles adjacent the inner side (the big toe side) of the foot.

It is another object of the present invention to provide a device that alleviates the symptoms of restless leg syndrome, restless arms, and foot and leg cramps and which can be easily and quickly attached to, and detached from, the individual's foot.

It is yet another object of the present invention to provide a device that alleviates the symptoms of restless leg syndrome, restless arms, and foot and leg cramps by contacting the sole of the foot and specifically applying pressure to the abductor hallucis and flexor hallucis brevis muscles.

It is yet another object of the present invention to provide a device that alleviates the symptoms of restless leg syndrome, restless arms, and foot and leg cramps wherein the application of pressure to the desired areas on the sole of the foot can be adjusted consonant with the severity and duration of the affliction.

It is yet another object of the present invention to provide a device that alleviates the symptoms of restless leg syndrome, restless arms, and foot and leg cramps wherein the application of pressure to the desired areas on the inner side of the foot can be adjusted consonant with the severity and duration of the affliction.

It is still yet another object of the present invention to provide a device that alleviates the symptoms of restless leg syndrome, restless arms, and foot and leg cramps wherein the application of pressure to the desired areas on the sole of the foot and on the inner side of the foot can be adjusted consonant with the severity and duration of the affliction.

These and other objects, features and advantages will become apparent to one skilled in the art upon a perusal of the following detailed description read in conjunction with the accompanying drawing figures and appended claims.

BRIEF DESCRIPTION OF THE SEVERAL VIEWS OF THE DRAWING

FIG. 7 is a top plan view of the device for alleviating the symptoms of restless leg syndrome, restless arms, and foot and leg cramps illustrating the layered or upraised structure of the pressure application pad;

FIG. 8 is a side elevational view of the device for alleviating the symptoms of restless leg syndrome, restless arms, and foot and leg cramps illustrating the layered or upraised structure of the pressure application pad;

FIG. 9 is a side elevational view of the device for alleviating the symptoms of restless leg syndrome, restless arms, and foot and leg cramps illustrating the contiguous disposition of the pressure application pad against the sole and/or the inner side of the foot, a right foot is illustrated, the drawing is numbered for use on a right foot;

DETAILED DESCRIPTION OF THE INVENTION

Illustrated in FIGS. 3 through 11 is a device 10 for relieving and alleviating the symptoms associated with restless leg syndrome, restless arms, and foot and leg cramps. Device 10 is lightweight, durable, easily washable, and storable, and can be quickly attached to, and detached, from the foot 12 of an individual as needed. Restless leg syndrome (RLS) is an affliction of the lower extremities, and it can be particularly exasperating during nighttime as the various symptoms of RLS can completely interfere with the ability of the individual to get an uninterrupted night's sleep. Because the symptoms of RLS often manifest themselves in the twitching and consequent muscle soreness of the leg and foot, both pharmaceutical and exercise means have been employed in order to relieve and alleviate the symptoms of RLS so that the individual can obtain a restful night's sleep.

Figure 1:
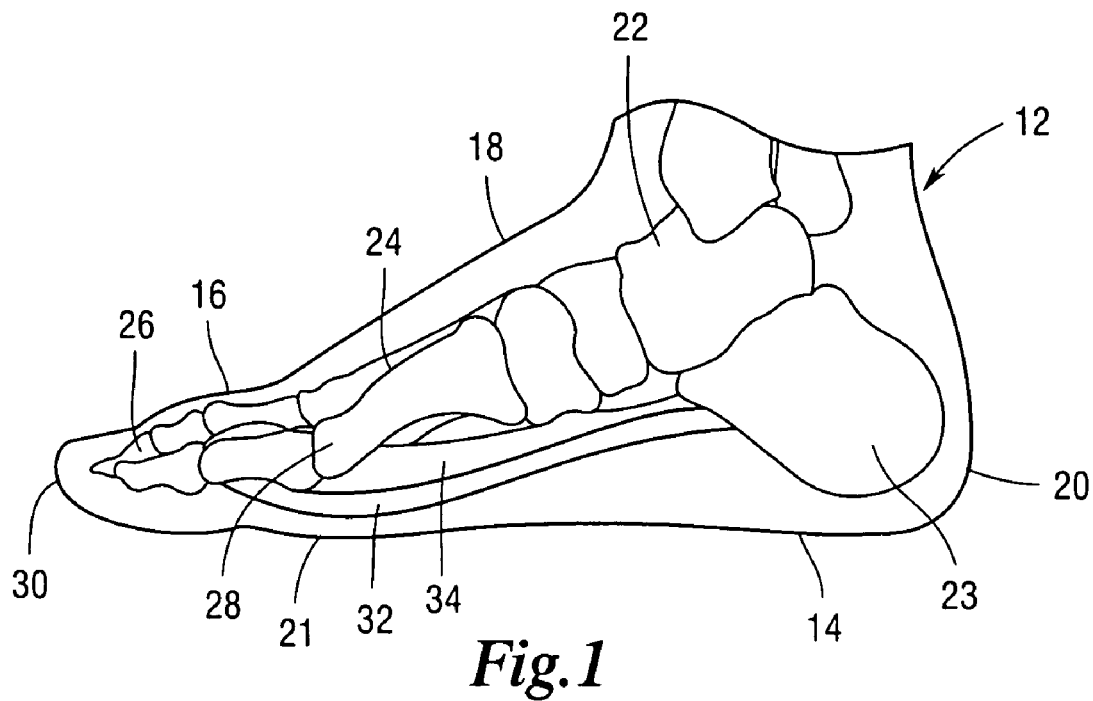
FIG. 1 is a side elevational view illustrating select bones and the muscles of the foot that are to be engaged by a device for alleviating the symptoms of restless leg syndrome, restless arms, and foot and leg cramps of the foot, a right foot is illustrated.
Figure 2:
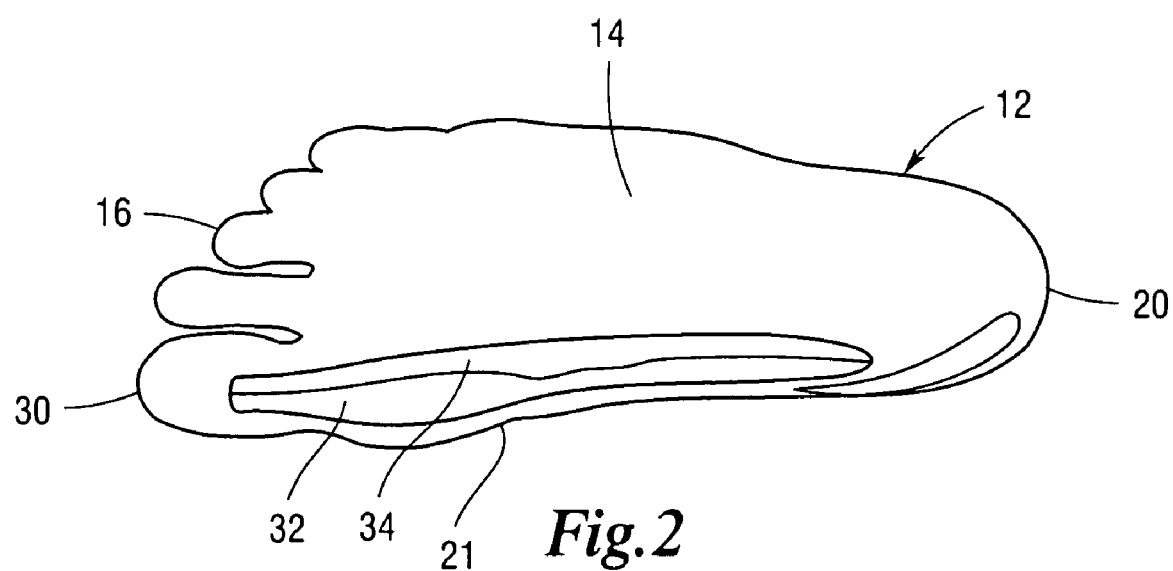
FIG. 2 is a bottom plan view illustrating select bones and the muscles of the foot that are to be engaged by a device for alleviating the symptoms of restless leg syndrome, restless arms, and foot and leg cramps of the foot, a left foot is illustrated.

Thus, a representative foot 12 is shown in FIGS. 1 and 2 that include a sole 14, toes 16, a foot upper side 18, a heel 20, and an inner side 21. In addition, for illustrative purposes, prominent bones are shown that include the talus 22, the calcaneus 23, the metatarsals 24, the phalanges 26 and the metatarsal head 28 that is the bony prominence immediately behind the big toe 30. While there are numerous tendons, ligaments, and muscles in foot 12, the muscles of foot 12 to which the present device 10 pertains are the muscle group that includes the medial, plantar and lateral edge of the flexor hallucis brevis muscle 32 and the abductor hallucis muscles 34. The crosspiece or cross bar 68 applies pressure to the side of the abductor hallucis muscles 34 and the flexor hallucis brevis muscles 32; and, the leg or stem 66 applies pressure to the bottom of the flexor hallucis brevis muscle 32 and the abductor hallucis muscles 34. Alleviation of the symptoms of RLS is obtained by the selective and adjustable application of pressure to these muscles 32 and 34 by device 10 of the present invention.

As shown in FIGS. 3 through 10, device 10 is more particularly a flexible or pliable foot relief pad 36 that is wrapped about and secured to foot 12 for providing relief as will be hereinafter described. It should be noted that device 10 is to be used when the individual is sitting down or recumbent, and is not to be used when the individual is ambulatory. Foot relief pad 36 includes a cloth wrap or cloth wrapping member 38 that is durable and washable and generally wear resistant. Cloth wrapping member 38 further includes a foot engaging portion 40 that is disposed beneath and contiguous to sole 14 of foot 12 and a foot securing portion 42 that is wrapped about or around upper side 18 of foot 12 for attachment, either directly or indirectly, to foot engaging portion 40. Foot engaging portion 40 and foot securing portion 42 are conjoined by a flexible fold or crease 44 that in effect serves as the demarcation between those portions 40 and 42, and also facilitates the wrapping of foot securing portion 42 about foot 12. In use, device 10 encompasses foot 12 and with foot engaging portion 40 being specifically positioned adjacent and contiguous to the area of sole 14 immediately behind metatarsal head 28 of big toe 30. Thus, cloth wrapping member 38 is further defined by a leading edge 46 that is aligned adjacent to the metatarsal head 28 of big toe 30 and a trailing edge 48 that is disposed toward heel 20 of foot 12 when device 10 is placed on foot 12 as shown in FIG. 9.

Figure 4:
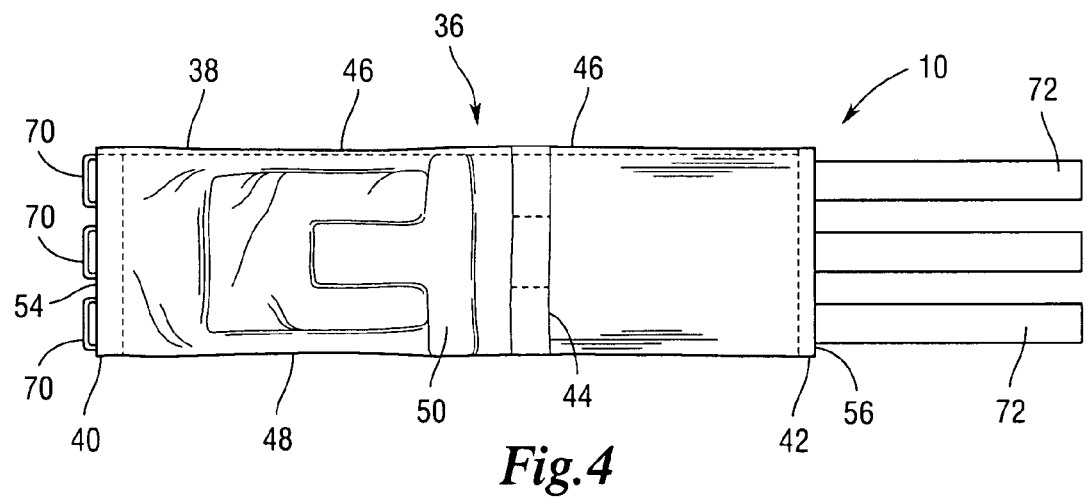
FIG. 4 is a bottom plan view of the device for alleviating the symptoms of restless leg syndrome, restless arms, and foot and leg cramps, the view is numbered for a left foot.

In FIG. 4, leading edge 46 and trailing edge 48 show device 10 ready for use on a left foot 12.

Figure 10:
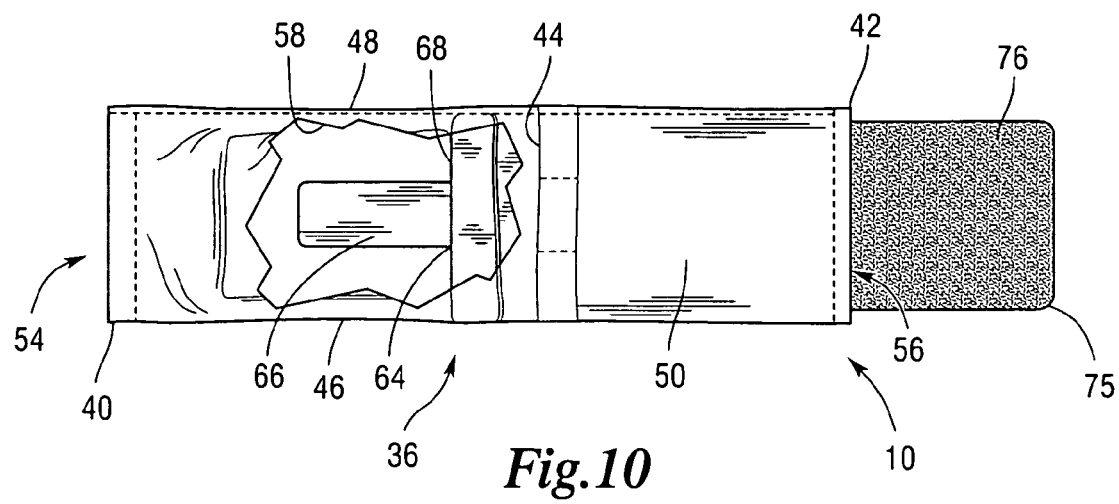
FIG. 10 is a bottom plan view of the device for alleviating the symptoms of restless leg syndrome, restless arms, and foot and leg cramps illustrating an alternative embodiment for the securement of the device about the foot, the drawing is numbered for use on a left foot.

In FIGS. 9 and 10, leading edge 46 and trailing edge 48 show device 10 ready for use on a right foot 12.

Figure 3:
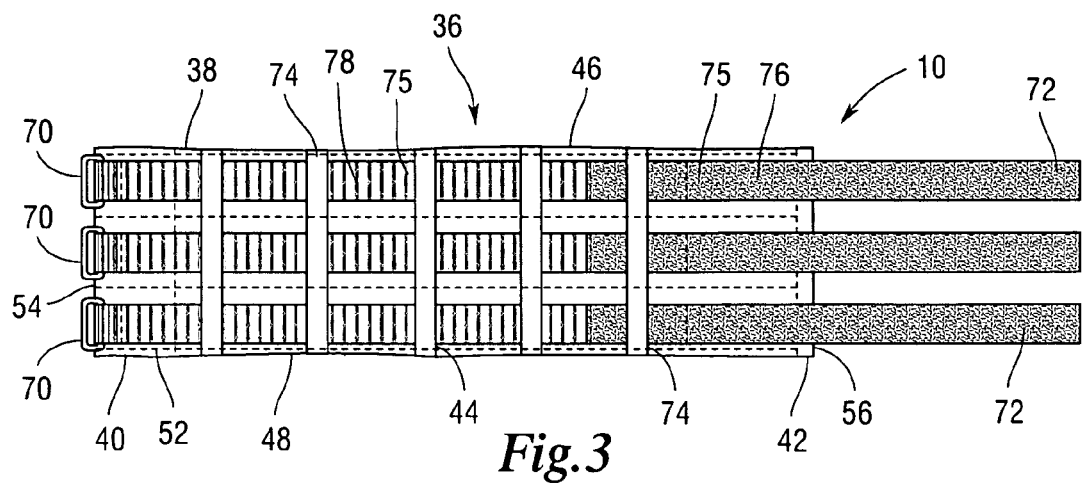
FIG. 3 is a top plan view of the device for alleviating the symptoms of restless leg syndrome, restless arms, and foot and leg cramps.
Figure 5:
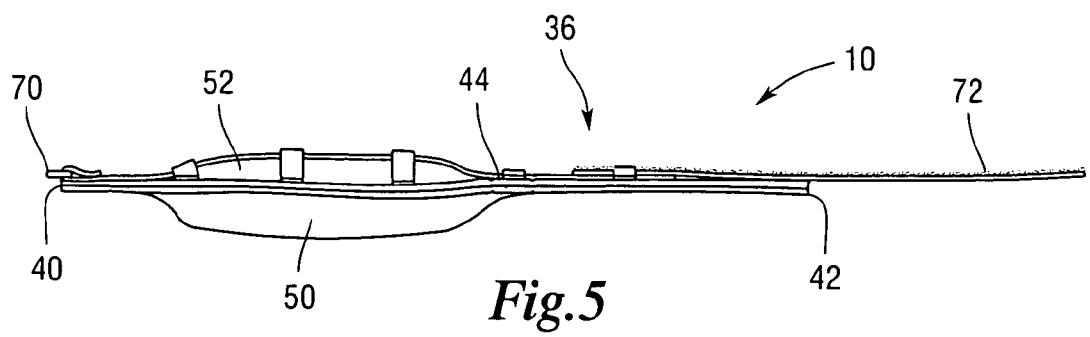
FIG. 5 is a side elevational view of the device for alleviating the symptoms of restless leg syndrome, restless arms, and foot and leg cramps.
Figure 6:
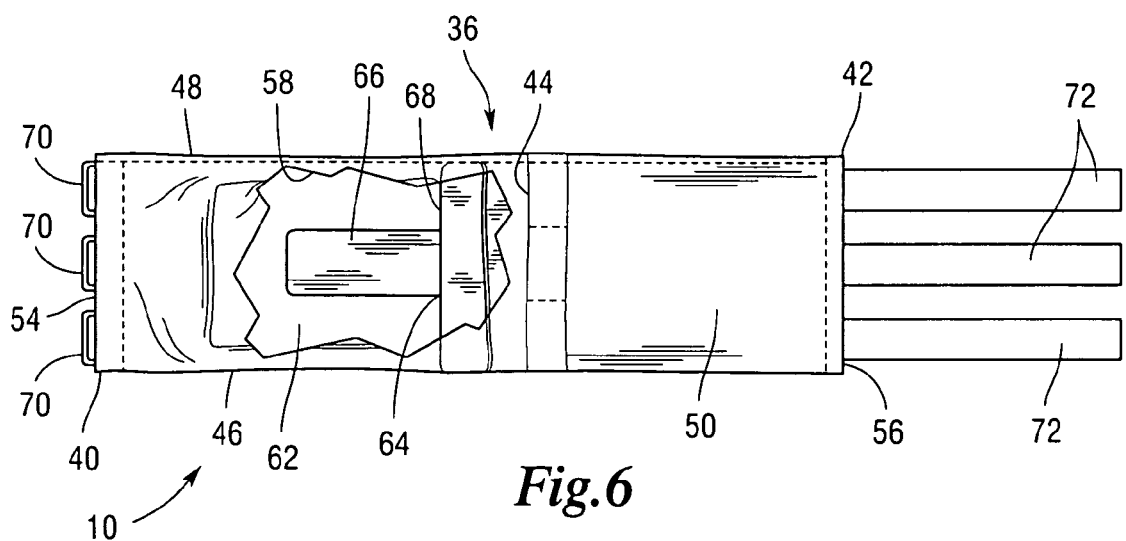
FIG. 6 is a bottom plan view of the device for alleviating the symptoms of restless leg syndrome, restless arms, and foot and leg cramps illustrating the foot engaging portion cut away to reveal the disposition of the pressure application pad, the view is numbered for use on a right foot.

In addition, as shown in FIGS. 3 through 5, foot engaging portion 40 and foot securing portion 42 combine to define a continuous inner surface 50 that faces inwardly and contacts foot 12, and an opposite continuous outer surface 52. Moreover, foot engaging portion 40 of foot relief pad 36 includes an attachment edge 54, and foot securing portion 42 includes a wrapping edge 56. When device 10 is placed on foot 12, wrapping edge 56 is brought into proximity with attachment edge 54 so that foot securing portion 42 can be attached to foot engaging portion 40.

As illustrated in FIGS. 6 through 9, foot engaging portion 40 defines a cavity 58; in effect cavity 58 is enclosed between continuous outer surface 52 and continuous inner surface 50. Enclosed or encased within cavity 58 is a multi-layered pressure application pad 60 for providing selective and adjustable pressure to the sole of foot 12 for relieving and alleviating the symptoms associated with RLS. Multi-layered pressure application pad 60 preferably includes two layers; one superposed on the other for creating an upraised pad or pad portion that effectively applies pressure to the above-described muscles 32 and 34 extending along inner side 21 and along sole 14 of foot 12. Thus, pressure application pad 60 includes a rectangular-shaped base pad or portion 62 that fills cavity 58. Rectangular-shaped pad 62 extends transverse within cavity 58 and to sole 14 of foot 12 when device 10 is mounted on and secured to foot 12. In addition, superposed on rectangular-shaped pad 62, either as an integral structural element or as a separate structural element, is a T-shaped pad or portion 64 that constitutes the upraised part of pressure application pad 62. T-shaped portion 64 includes a leg or stem 66 that extends along the body of rectangular-shaped pad 62, and also extends transverse to sole 14 of foot 12, and a crosspiece or cross bar 68 that is adjoined to and perpendicular to stem 66 of T-shaped portion 64. When device 10 is to be mounted to foot 12, leading edge 46 of foot relief pad 36 is generally aligned with metatarsal head 28 and crosspiece 68 is aligned with inner side 21 of foot 12 so that crosspiece 68 in particular can apply pressure to those aforementioned muscles 32 and 34 that extend along inner side 21 of foot 12. All the aforedescribed elements of pressure application pad 60 are preferably composed of heavy, high-density foam. While the elements of pressure application pad 60 are composed of high-density foam, pad 60 is somewhat pliable so that pad 60, and especially T-shaped portion 64, can conform to the curvature of inner side 21 of foot 12. In addition, each element of pressure application pad 60—rectangular-shaped portion 62, crosspiece 68 and stem 66—can be separate structural elements; or rectangular-shaped portion 62 and T-shaped portion 64 can be separate structural elements; or, finally, rectangular-shaped base pad 62 and T-shaped portion 64 can be configured from an integral one-piece structure. The primary feature that must be maintained, however, is the upraised configuration of T-shaped portion 64 for abutting and applying pressure to muscles 32, 34 at inner side 21 of foot 12, and leg or stem 66 for abutting and applying pressure to the bottom of muscles 32, 34 of sole 14 of foot 12.

As shown in FIGS. 3 through 6, device 10 includes a securement means for comfortably but securely attaching device 10 onto foot 12 of the individual. More importantly, the securement means is adjustable so that different amounts of pressure on the above-described muscles 32 and 34 can be obtained. The securement means of FIGS. 3 through 6 includes a plurality of eyelets or rings 70 pivotally attached to attachment edge 54 of foot engaging portion 40. Extending from each eyelet 70 and then extending along continuous outer surface 52 of both foot engaging portion 40 and foot securing portion 42 of wrapping member 38 is a flexible strap 72. Flexible straps 72 incorporate separable hook and loop type fasteners 75, such as Velcro® material or other suitable fastener, with a portion of each length of each strap 72 comprising first portion 76 of either hook or loop material, and the remaining portion comprising a second portion of the other of hook or loop material 78. Each strap 72 extends past wrapping edge 56 of foot securing portion 42 to insure that straps 72 will encompass foot 12 with enough additional length to provide for their adjustment so that the pressure applied by pressure application pad 60 can be adjusted as desired by the individual. In order to maintain the generally longitudinal extension of straps 72, straps 72 pass beneath a pair of spaced apart retaining members 74 mounted to outer surface 52 and extending transverse to the extension of straps 72. When device 10 is placed on the individual's foot 12 with foot engaging portion 40 located beneath and contiguous with sole 14 of foot 12, straps 72 wrap around foot 12 and are able to loop back upon themselves for securement. Since each strap 72 is securable independent of the other straps 72, each strap 72 can be secured tighter or looser than the other straps 72. This provides for a more selective application of pressure to different areas of sole 14 of foot 12, and thus to the specific muscles 32 and 34 of the aforementioned group of muscles so that one area of sole 14 and inner side 21 can have more pressure applied to it than an adjacent area.

Figure 11:
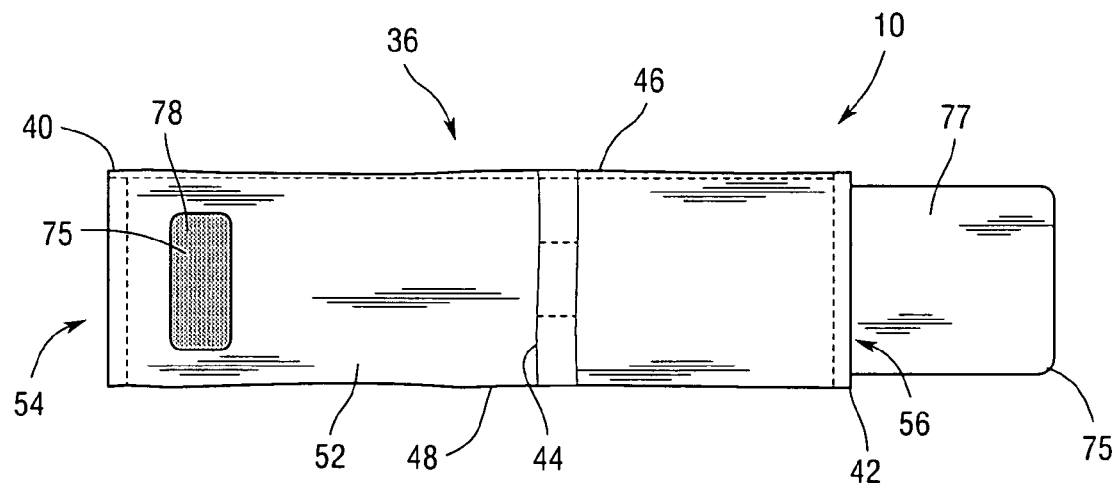
FIG. 11 is a top plan view of the device for alleviating the symptoms of restless leg syndrome, restless arms, and foot and leg cramps illustrating an alternative embodiment for the securement of the device about the foot.

FIGS. 10 and 11 illustrate an alternative securement means that does not require straps 72 of FIGS. 3 through 6. In FIG. 10 the length of foot securing portion 42 has been extended so that it can fully encompass and overlap part of foot engaging portion 40 for securement thereto. In addition, hook and loop fastener 75 may have first portion 76 of hook and loop fastener 75 comprising either the hook or the loop portion of fastener 75. First portion 76 is attached to inner surface 50 of foot securing portion 42 adjacent wrapping edge 56. Hook and loop fastener 75 may also have second portion 78 of hook and loop fastener 75 comprising the other of the hook or the loop portion of fastener 75. Second portion 78 of hook and loop fastener 75 is attached to outer surface 52 of foot engaging portion 40 adjacent attachment edge 54. The hook and loop fastener material being attached or affixed to securing portion 42 and engaging portion 40 simplifies attachment of the device to the foot. Thus, in order to attach device 10 of FIG. 10 to foot 12, foot securing portion 42 is simply wrapped about foot 12 until it overlaps foot engaging portion 40 whereupon first portion 76 of hook and loop fastener 75 is pressed against second portion 78 of hook and loop fastener 75 thereby securing foot engaging portion 40 to foot securing portion 42 and securing foot relief pad 36 to foot 12. Second portion 78 is secured to outer surface 52 of foot engaging portion 40. First portion 76 has back surface 77 that does not have fasteners thereon.

Figure 12:
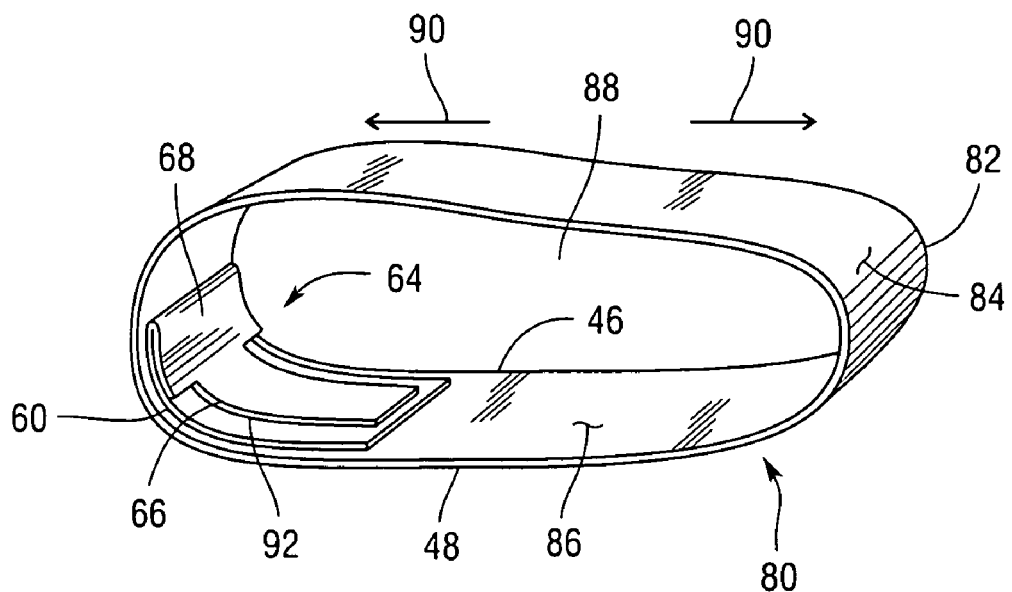
FIG. 12 is a perspective view of an alternative embodiment for the device for alleviating the symptoms of restless leg syndrome, restless arms, and foot and leg cramps and which includes a supporting portion for placement on the foot in the form of an elastic band with the pressure application affixed pad to the inside surface of the band for applying pressure to selected areas on the sole of the foot and/or on the inner side of the foot, the drawing is numbered for use on a right foot; and, FIG. 13 is a perspective view of a second alternative embodiment for the device for alleviating the symptoms of restless leg syndrome, restless arms, and foot and leg cramps and which includes a shoe insert for placement within a shoe and the pressure application pad affixed thereto so that the pad can apply pressure to selected areas of the sole of the foot and/or on the inner side of the foot, the drawing is numbered for use on a right foot.
Figure 13:
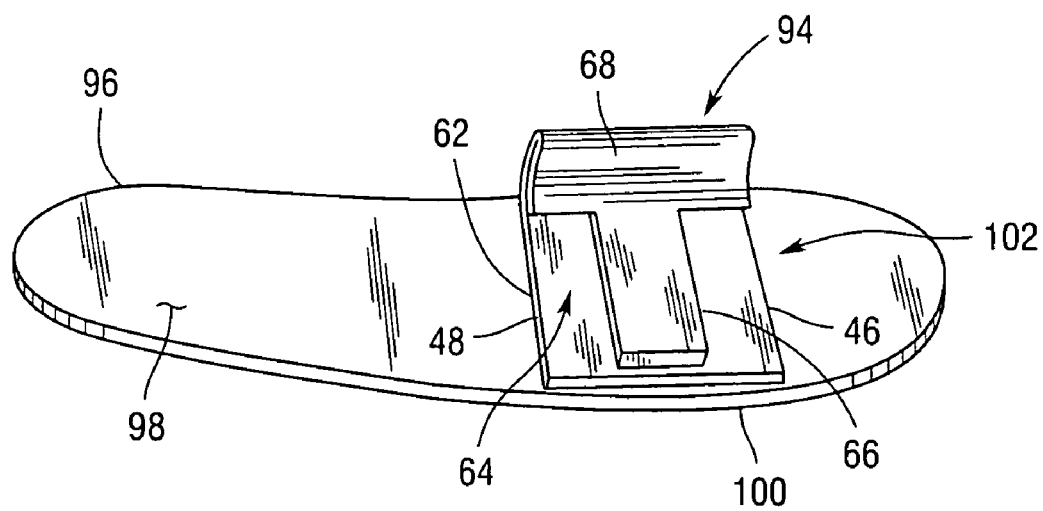

Illustrated in FIGS. 12 and 13 are alternative embodiments for device 10 that include pressure application pad 60, but different supporting structures for pad 60. Specifically, FIG. 12 includes a foot pressure positioning means in the form of a lightweight, portable, removable supporting portion 80 that is slipped onto foot 12 and then adjusted so that pad 60 is properly positioned for applying pressure to muscles 32 and 34. Supporting portion 80 includes a flexible elastic band 82, and elastic band 82 defines a continuous external surface 84 and an opposite continuous internal surface 86. When supporting portion 80 is disposed on foot 12 of the individual, elastic band 82 will expand and contract as necessary to fit onto foot 12, and continuous internal surface 86 will abut or be contiguous to foot 12 of the individual. As shown in FIG. 12, supporting portion 80 has a flattened cylindrical shape and further defines a foot aperture 88 through which the individual's foot 12 is inserted for using supporting portion 80. Supporting portion 80 can be adjusted along the length of foot 12, and, in addition, the flattened cylindrical shape allows for the radial slidable adjustment of supporting portion 80 about foot 12. Directional arrows 90 indicate that supporting portion 80 can be rolled in either direction (left/right or medial/lateral) for properly aligning T-shaped portion 64 and stem 66 of pad 60 with the appropriate muscles 32 and 34. Pad 60 is affixed or attached to continuous internal surface 86, and pad 60 serves as the pressure application portion or pressing portion 92 of supporting portion 80.

In use the individual's foot 12 is slipped through foot aperture 88 of elastic band 82, and then elastic band 82 is pushed back on foot 12 so that crosspiece 68 generally aligns with inner side 21 of foot 12, and stem 66 extends transverse to sole 14 of foot 12. Supporting portion 80 is slidably positionable and repositionable upon foot 12; and some radial adjustment of elastic band 82 on foot 12 may be necessary to properly position stem 66 and crosspiece 68 so that stem 66 is aligned for applying pressure to the underside of flexor hallucis brevis muscle 32 and abductor hallucis muscles 34, and crosspiece 68 is aligned for applying pressure to the side of abductor hallucis muscles 34 and flexor hallucis brevis muscles 32. The contraction of elastic band 82 about and against foot 12 causes pressing portion 92, which includes pad 60, stem 66 and crosspiece 68, to continuously press against the aforesaid muscles 32 and 34 to thereby provide relief from the symptoms of RLS.

FIG. 13 illustrates a second alternative embodiment for the device shown in FIGS. 1 through 11. Specifically, FIG. 13 illustrates a supporting portion 94 that is a lightweight, portable, removable shoe insert 96 for disposition within a shoe and upon the shoe insole for applying pressure to muscles 32 and 34 as aforedescribed. Shoe insert 96 is preferably rectangular-shaped and includes an upper surface 98 and an opposite lower surface 100. Shoe insert 96 should have some flexibility to allow it to adapt and conform to the particular insole of the shoe. While shoe insert 96 is placed within the shoe and on the insole of the shoe, insert 96 does not have to cover or be commensurate in length and breadth with the insole to apply pressure to foot 12; shoe insert 96 generally needs to be coextensive with that part of sole 14 of foot 12 that includes hallucis brevis muscle 32 and abductor hallucis muscles 34. Affixed or secured to upper surface 98 is pressure application pad 60. Pad 60 is located upon upper surface 98 so that stem 66 and crosspiece 68 can easily be aligned with the corresponding hallucis brevis muscle 32 and abductor hallucis muscles 34. Pad 60, and especially stem 66 and crosspiece 68, specifically serves as pressing portion 102 for supporting portion 94 in order to relieve the symptoms associated with RLS.

It should be understood from the foregoing that while particular embodiments of the invention have been shown and described, numerous modifications, alterations and variations are possible and practicable to those skilled in the art without departing from the spirit of the invention or the scope of the appended claims.

What is claimed is:

1. A device to alleviate the symptoms of restless leg syndrome, restless arms, and foot and leg cramps and which is wrapped around a foot of an individual so that pressure can be applied to specific areas on a sole of said foot, comprising:
    a flexible cloth wrap that includes a foot securing portion joined by a fold to a foot engaging portion, said foot securing portion and said foot engaging portion including a continuous outer surface and an opposite continuous inner surface, said foot engaging portion including a cavity;
    a multi-layered pad disposed within said cavity, said multi-layered pad having a base portion and an upraised portion disposed on said base portion, said upraised portion having a leg and a crosspiece, wherein said leg and said crosspiece are at a substantially perpendicular angle, said multi-layered pad being capable of applying pressure to specific areas on the sole of said foot; and,
    securement means extending along said continuous outer surface of said foot engaging portion and said foot securing portion for securing said foot engaging portion contiguous to said sole of said foot and said foot securing portion about the upper side of said foot whereupon pressure is applied by said multi-layered pad to specific areas on said sole of said foot, said leg of said upraised portion positioned to exert pressure primarily against the flexor hallucis brevis muscle of the foot, said crosspiece of said upraised portion positioned to exert pressure primarily against the abductor hallucis muscle of the foot.

2. The device to alleviate the symptoms of restless leg syndrome, restless arms, and foot and leg cramps of claim 1, wherein said foot engaging portion includes an attachment end.

3. The device to alleviate the symptoms of restless leg syndrome, restless arms, and foot and leg cramps of claim 2, wherein said foot securing portion includes a wrapping end.

4. The device to alleviate the symptoms of restless leg syndrome, restless arms, and foot and leg cramps of claim 3, wherein said base portion comprises a rectangular-shaped pad that extends across said sole of said foot when said foot engaging portion is disposed contiguous to said sole of said foot.

5. The device to alleviate the symptoms of restless leg syndrome, restless arms, and foot and leg cramps of claim 4, wherein said leg and said crosspiece of said upraised portion forms a T-shaped pad that abuts an inner edge of said foot when said foot engaging portion is disposed contiguous to said sole of said foot.

6. The device to alleviate the symptoms of restless leg syndrome, restless arms, and foot and leg cramps of claim 5, wherein said crosspiece extending along the inner side of said foot.

7. The device to alleviate the symptoms of restless leg syndrome, restless arms, and foot and leg cramps of claim 6, wherein said securement means includes a plurality of loops secured to the attachment end of said foot engaging portion.

8. The device to alleviate the symptoms of restless leg syndrome, restless arms, and foot and leg cramps of claim 7, wherein said securement means further includes a plurality of flexible straps that extend from said loops across said continuous outer surface and past said wrapping end of said foot securing portion so that said straps can wrap around said foot and loop back upon themselves for securing said foot engaging portion beneath said sole of said foot and said foot securing portion about an upper side of said foot.

9. A foot relief pad for alleviating the symptoms of restless leg syndrome, restless arms, and foot and leg cramps by applying pressure to a group of muscles extending along an inner side of a foot, comprising:
 a cloth wrapping member that includes a foot securing portion adjoined to a foot engaging portion by a flexible fold;
 a continuous outer surface extending along said foot engaging portion and said foot securing portion;
 a continuous inner surface extending along said foot engaging portion and said foot securing portion that is opposite of said continuous outer surface, said foot engaging portion including a cavity;
 a pressure application pad contained within said cavity and having a base portion and an upraised T-shaped portion disposed on said base portion, said upraised T-shaped portion having a leg and a crosspiece and being configured for contacting the inner side of said foot;
 securement means extending along said continuous outer surface of said foot engaging portion and said foot securing portion for encompassing said foot so that said foot engaging portion is secured contiguous to a sole of said foot and said foot securing portion is disposed about the upper side of said foot whereupon the upraised T-shaped portion of said pressure application pad abuts the inner side of said foot for the application of pressure there against, said upraised T-shaped portion being positioned to exert the majority of the total pressure exerted by said pad against the foot; and,
 said leg of said upraised T-shaped portion being positioned to exert pressure primarily against the flexor hallucis brevis muscle of the foot, said crosspiece of said upraised T-shaped portion being positioned to exert pressure primarily against the abductor hallucis muscle of the foot in order to alleviate the symptoms of restless leg syndrome, restless arms, and foot and leg cramps.

10. The foot relief pad for alleviating the symptoms of restless leg syndrome, restless arms, and foot and leg cramps of claim 9, wherein said foot engaging portion includes an attachment end.

11. The foot relief pad for alleviating the symptoms of restless leg syndrome, restless arms, and foot and leg cramps of claim 10, wherein said foot securing portion includes a wrapping end.

12. The foot relief pad for alleviating the symptoms of restless leg syndrome, restless arms, and foot and leg cramps of claim 11, wherein said base portion comprises a generally rectangular-shaped portion that extends transverse to said sole of said-foot when said foot engaging portion is disposed beneath said sole of said foot.

13. The foot relief pad for alleviating the symptoms of restless leg syndrome, restless arms, and foot and leg cramps of claim 12, wherein said crosspiece abuts and applies pressure to the inner side of said foot.

14. The foot relief pad for alleviating the symptoms of restless leg syndrome, restless arms, and foot and leg cramps of claim 13, wherein said securement means includes a plurality of loops that are pivotally secured to said attachment end of said foot engaging portion.

15. The foot relief pad for alleviating the symptoms of restless leg syndrome, restless arms, and foot and leg cramps of claim 14, wherein said securement means further includes a plurality of flexible straps that extend from said loops along said continuous outer surface and past said wrapping end of said foot securing portion so that said straps can wrap around said foot and loop back upon themselves at said attachment end for securing said foot engaging portion continuous to said sole of said foot and said foot securing portion about the support side of said foot.

16. A foot relief pad for alleviating the symptoms of restless leg syndrome, restless arms, and foot and leg cramps through the application of pressure to a group of muscles extending along an inner side of a foot and across a sole of the foot, comprising:
 a flexible cloth wrapping member that includes a foot engaging portion and a foot securing portion with said foot engaging portion disposed beneath said sole of said foot and said foot securing portion disposed around an upper side of said foot;
 a continuous outer surface extending along said foot engaging portion and said foot securing portion;
 a continuous inner surface extending along said foot engaging portion and said foot securing portion and which is opposite of said continuous outer surface; said foot engaging portion including a cavity;
 a layered pressure application pad encased within said cavity and disposed in abutting relationship to said sole of said foot, said layered pressure application pad having a base portion and an upraised portion disposed on said base portion, said upraised portion having a leg and a crosspiece, wherein said leg and said crosspiece are at a substantially perpendicular angle, said layered pressure application pad being configured to apply pressure to the group of muscles extending along the inner side of said foot and across the sole of said foot; and,
 securement means for securing said foot securing portion to said foot engaging portion so that said foot engaging portion is positioned beneath and contiguous to said sole of said foot and said foot securing portion is wrapped around said upper side of said foot and then secured to said foot engaging portion whereupon said layered pressure application pad is located in abutting relationship to said inner side of said foot and to said sole of said foot so that pressure can be applied by said pressure application pad to said inner side of said foot and said sole of said foot, said upraised portion of said pad being positioned to exert the majority of the total pressure exerted by said pad against the foot; and
 said leg of said upraised portion being positioned to exert pressure primarily against the flexor hallucis brevis muscle of the foot, said crosspiece of said upraised portion of said pad being positioned to exert pressure primarily against the abductor hallucis muscle of the foot for alleviating of the symptoms of restless leg syndrome, restless as arms, and foot and leg cramps.

17. The foot relief pad for alleviating the symptoms of restless leg syndrome, restless arms, and foot and leg cramps of claim 16, wherein said base portion comprises a generally rectangular-shaped portion that extends transverse to said sole of said foot when said foot engaging portion is positioned beneath said sole of said foot.

18. The foot relief pad for alleviating the symptoms of restless leg syndrome, restless arms, and foot and leg cramps of claim 17, wherein said leg and said crosspiece of said upraised portion forms a T-shaped portion that abuts said inner side of said sole of said foot for applying pressure to the group of muscles that extend along said inner side when said foot engaging portion is disposed beneath said sole of said foot.

19. A device for alleviating the symptoms of restless leg syndrome, restless arms, and foot and leg cramps by the application of pressure against the hallucis brevis muscle and the abductor hallucis muscles of a foot, comprising:

a supporting portion;

a pressing portion secured to said supporting portion, said pressing portion including a pressure application pad having a base portion and an upraised portion disposed on said base portion, said upraised portion having a leg and a crosspiece, wherein said leg and said crosspiece are at a substantially perpendicular angle;

said supporting portion supporting said pressing portion in an operative position to exert pressure against said foot;

said upraised portion of said pressure application pad being positioned to exert the majority of the total pressure exerted by said pressure application pad against the foot; and, said leg of said upraised portion being positioned to exert pressure primarily against the flexor hallucis brevis muscle of the foot and said crosspiece of said upraised portion being positioned to exert pressure primarily against the abductor hallucis muscle of said foot for relieving the symptoms of restless leg some syndrome, restless arms, and foot and leg cramps.

20. A method to alleviate the symptoms of restless leg syndrome, restless arms, and foot and leg cramps, comprising the steps of:

providing a supporting portion;

providing a pressing portion that is attached to said supporting portion, said pressing portion including a pressure application pad having a base portion and an upraised portion disposed on said base portion, said upraised portion having a leg and a crosspiece, said leg and said crosspiece are at a substantially perpendicular angle;

placing said supporting portion on a foot of an individual to exert pressure against the foot;

positioning said pressure application pad such that said upraised portion exerts the majority of the total pressure exerted by said pad against the foot; and, positioning said leg of said upraised portion to exert pressure primarily against the flexor hallucis brevis muscle of the foot, and positioning said crosspiece of said upraised portion of said pad to exert pressure primarily against the abductor hallucis muscle of the foot in order to alleviate the symptoms of restless leg syndrome, restless arms, and foot and leg cramps.

21. A device for applying pressure to specific areas of a foot of an individual, the device comprising:

a flexible wrap that includes an outer surface and a foot securing portion adjoined to a foot engaging portion, said foot engaging portion including a cavity;

a pressure application pad contained within said cavity;

said foot engaging portion being connectable to said foot securing portion to position said foot engaging portion beneath and contiguous to a sole of the foot while said foot securing portion is wrapped around an upper side of the foot and then secured to the foot engaging portion to place said pressure application pad in an abutting relationship to an inner side of the foot and to the sole of the foot and to apply pressure to the inner side of the foot and to the sole of the foot;

said pressure application pad having a base portion and an upraised portion disposed on said base portion, said upraised portion having a leg and a crosspiece, said leg extending transversely along the sole of the foot, said crosspiece extending about perpendicularly from an end of the leg to extend along the inner side of the foot, said upraised portion being positioned to exert the majority of the total pressure exerted by said pad against the foot;

said leg being positioned to abut and apply pressure directed to the flexor hallucis brevis muscle primarily at the bottom of the foot; and, said crosspiece being positioned to abut and primarily apply pressure directed to the abductor hallucis muscle, said crosspiece being positioned to apply pressure primarily to the inner side of the foot.

22. The device of claim 21, further comprising a flexible fold adjoining said foot engaging portion to said foot securing portion.

23. The device of claim 21, further comprising a flexible fold.

24. The device of claim 21, wherein said foot engagement portion includes an attachment end.

25. The device of claim 21, wherein said foot securing portion includes a wrapping end.

26. The device of claim 21, wherein said base pad being shaped to be positioned on and extend transversely along the sole of the foot when said pressure application pad is mounted on and secured to the foot, said upraised portion extending along the base pad to extend transversely along the sole of the foot.

27. The device of claim 21, wherein said crosspiece being adjoined to said leg, the combined crosspiece and leg being T-shaped.

28. The device of claim 21, further comprising a plurality of loops pivotally secured to an attachment end of the foot engaging portion to secure said foot engaging portion to said foot securing portion.

29. The device of claim 21, further comprising a plurality of loops pivotally secured to an attachment end of the foot engaging portion and a plurality of flexible straps that extend from said loops along said outer surface and past a wrapping edge of said foot securing portion so that said straps can wrap around the foot and loop back upon themselves at said attachment end for securing said foot engaging portion contiguous to the sole of the foot and said foot securing portion about an upper side of the foot.

30. A pressure application pad for providing selective and adjustable pressure to a sole of a foot comprising:

a base portion;

an upraised portion disposed on said base portion, said upraised portion having a leg and a crosspiece, said leg extending transversely along the sole of the foot, said crosspiece extending about perpendicularly from an end of the leg to extend along the inner side of the foot;

said leg being positioned to abut and primarily apply pressure directed to the flexor hallucis brevis muscle at the bottom of the foot; and, said crosspiece being positioned to abut and primarily apply pressure directed to the abductor hallucis muscle, said crosspiece being positioned to apply pressure primarily to the inner side of the foot.

31. The pressure application pad of claim 30, wherein said leg and said crosspiece being configured from an integral one-piece structure.

32. The pressure application pad of claim 30, wherein said pad being constructed of pliable, high-density foam.

33. The pressure application pad of claim 30, wherein said crosspiece being adjoined to said leg.

34. The pressure application pad of claim 30, said crosspiece being adjoined to said leg, the combined crosspiece and leg being T-shaped.

35. A multi-layered pressure application pad for providing selective and adjustable pressure to a sole of a foot comprising:
- a first layer that is a base pad, said base pad being shaped to be positioned on and extend transversely along the sole of the foot when said pressure application pad is mounted on and secured to the foot;
- a second layer superposed on said first layer to create an upraised pad portion, said upraised pad portion having a leg and a crosspiece, said leg extending along the base pad to extend transversely along the sole of the foot, said crosspiece extending about perpendicularly from an end of the leg along the base pad to extend along the inner side of the foot;
- said crosspiece of said upraised pad portion positioned to abut and apply pressure directed primarily to the abductor hallucis muscle, said crosspiece positioned to primarily apply pressure to the inner side of the foot;
- said leg of said upraised pad portion positioned to abut and apply pressure directed to the flexor hallucis brevis muscle primarily at the bottom of the foot; and, said upraised pad portion being positioned to exert the majority of the total pressure exerted by said pad against the foot.

36. The pressure application pad of claim 35, wherein said base pad being rectangular shaped.

37. The pressure application pad of claim 35, wherein said base pad and said upraised pad portion being configured from an integral one-piece structure.

38. The pressure application pad of claim 35, wherein said pad being constructed of pliable, high-density foam.

39. The pressure application pad of claim 35, wherein said crosspiece being adjoined to said leg.

40. The pressure application pad of claim 35, wherein said crosspiece being adjoined to said leg, said upraised pad portion being T-shaped.

41. A shoe insert having a pressure application pad for providing selective and adjustable pressure to a sole of a foot comprising:
- an insole having an upper surface, said insole being positionable within a shoe;
- said pressure application pad being positioned on said upper surface of said insole;
- said pressure application pad having a base portion and an upraised portion disposed on said base portion, said upraised portion having a leg and a crosspiece, said leg extending transversely along the sole of the foot when the foot is inserted in the shoe, said crosspiece extending about perpendicularly from an end of the leg to extend along the inner side of the foot when the foot is inserted in the shoe;
- said leg being positioned to abut and primarily apply pressure directed to the flexor hallucis brevis muscle at the bottom of the foot; and,
- said crosspiece being positioned to abut and primarily apply pressure directed to the abductor hallucis muscle, said crosspiece being positioned to apply pressure primarily to the inner side of the foot.

42. The shoe insert of claim 41, wherein said leg and said crosspiece being configured from an integral one-piece structure.

43. The shoe insert of claim 41, wherein said pad being constructed of pliable, high-density foam.

44. The shoe insert of claim 41, wherein said crosspiece being adjoined to said leg.

45. The shoe insert of claim 41, wherein said crosspiece being adjoined to said leg, the combined crosspiece and leg being T-shaped.

46. The shoe insert of claim 41, wherein said upraised portion of said pad being positioned to exert the majority of the total pressure exerted by said pad against the foot.

47. A method to alleviate the symptoms of restless leg syndrome, restless arms, and foot and leg cramps, comprising:
- providing a pressure application pad having an upraised portion having a leg and crosspiece;
- providing a wrapping member for encasing said pressure application pad, said wrapping member having multiple adjustable straps for securing said wrapping member and said pressure application pad;
- placing and securing said pressure application pad on the foot of an individual with said wrapping member, said leg of said pressure application pad being positioned to abut and primarily apply pressure directed to the flexor hallucis brevis muscle primarily at the bottom of the foot, said crosspiece of said pressure application pad being positioned to abut and primarily apply pressure directed to the abductor hallucis muscle primarily at the inner side of the foot; and,
- adjusting said multiple adjustable straps to selected magnitudes of tightness to adjustably vary the pressure exerted by said leg against said flexor hallucis brevis muscle and by said crosspiece against said abductor hallucis muscle to alleviate the symptoms of restless leg syndrome, restless arms, and foot and leg cramps.

* * * * *

UNITED STATES PATENT AND TRADEMARK OFFICE
CERTIFICATE OF CORRECTION

| | | |
|---|---|---|
| PATENT NO. | : 7,753,867 B2 | Page 1 of 1 |
| APPLICATION NO. | : 11/307052 | |
| DATED | : July 13, 2010 | |
| INVENTOR(S) | : Mary M. Sorg | |

It is certified that error appears in the above-identified patent and that said Letters Patent is hereby corrected as shown below:

Column 4, line 5, "left foot" should be changed to --right foot--.

Column 8, line 65, "inner edge" should be changed to --inner side--.

Column 10, line 65, delete the text "as".

Column 11, line 35, delete the text "some".

Signed and Sealed this
Fourteenth Day of August, 2012

David J. Kappos
*Director of the United States Patent and Trademark Office*